United States Patent
Gonzalez et al.

(10) Patent No.: US 9,375,439 B2
(45) Date of Patent: Jun. 28, 2016

(54) SMALL MOLECULES THAT PROMOTE SKIN REGENERATION

(71) Applicant: INTERNATIONAL STEM CELL CORPORATION, Carlsbad, CA (US)

(72) Inventors: Rodolfo Gonzalez, Carlsbad, CA (US); Maxim Poustovoitov, Carlsbad, CA (US); Ruslan Semechkin, Carlsbad, CA (US)

(73) Assignee: International Stem Cell Corporation, Carlsbad, CA (US)

( * ) Notice: Subject to any disclaimer, the term of this patent is extended or adjusted under 35 U.S.C. 154(b) by 0 days.

(21) Appl. No.: 14/150,616

(22) Filed: Jan. 8, 2014

(65) Prior Publication Data

US 2014/0309195 A1  Oct. 16, 2014

Related U.S. Application Data

(60) Provisional application No. 61/750,714, filed on Jan. 9, 2013.

(51) Int. Cl.

| | |
|---|---|
| *A61K 31/155* | (2006.01) |
| *A01N 37/52* | (2006.01) |
| *A61K 31/66* | (2006.01) |
| *A61K 31/18* | (2006.01) |
| *A61K 31/192* | (2006.01) |
| *A61K 31/4168* | (2006.01) |
| *A61K 31/4174* | (2006.01) |
| *A61K 31/454* | (2006.01) |
| *A61K 31/4709* | (2006.01) |
| *A61K 31/4745* | (2006.01) |
| *A61K 31/519* | (2006.01) |
| *A61K 31/5377* | (2006.01) |
| *A61K 31/5575* | (2006.01) |
| *A61K 31/407* | (2006.01) |
| *A61K 31/557* | (2006.01) |

(52) U.S. Cl.
CPC .............. *A61K 31/66* (2013.01); *A61K 31/155* (2013.01); *A61K 31/18* (2013.01); *A61K 31/192* (2013.01); *A61K 31/407* (2013.01); *A61K 31/4168* (2013.01); *A61K 31/4174* (2013.01); *A61K 31/454* (2013.01); *A61K 31/4709* (2013.01); *A61K 31/4745* (2013.01); *A61K 31/519* (2013.01); *A61K 31/5377* (2013.01); *A61K 31/557* (2013.01); *A61K 31/5575* (2013.01)

(58) Field of Classification Search
CPC ... A61K 31/155; A61K 31/18; A61K 31/192; A61K 31/407; A61K 31/4168; A61K 31/4174; A61K 31/454; A61K 31/4709; A61K 31/4745; A61K 31/519; A61K 31/5377; A61K 31/557; A61K 31/5575; A61K 31/66
USPC ........ 514/119, 233.5, 234.2, 262.1, 280, 312, 514/323, 386, 400, 569, 573, 604, 637
See application file for complete search history.

(56) References Cited

U.S. PATENT DOCUMENTS

| | | |
|---|---|---|
| 2007/0203234 A1 | 8/2007 | Schnellmann et al. |
| 2007/0218549 A1 | 9/2007 | Mansbridge et al. |
| 2007/0243158 A1 | 10/2007 | Ronfard et al. |
| 2009/0053290 A1 | 2/2009 | Sand et al. |
| 2012/0264218 A1 | 10/2012 | Lin et al. |
| 2013/0165463 A1* | 6/2013 | Gurtner et al. ................ 514/275 |
| 2014/0072613 A1* | 3/2014 | Lander et al. ................ 424/446 |

FOREIGN PATENT DOCUMENTS

WO    WO 2012/030919 A2    3/2012

OTHER PUBLICATIONS

Erttmann, Saskia F. et al.: "*PGD2 and PGE2 regulated gene expression of Prx 6 in primary macrophages via Nrf2*,"; Free Radic Biol Med, May 27, 2011, vol. 51, pp. 626-640.
International Search Report regarding PCT/US2014/010741, Mar. 25, 2014.

* cited by examiner

*Primary Examiner* — My-Chau T Tran
(74) *Attorney, Agent, or Firm* — DLA Piper LLP (US)

(57) ABSTRACT

Provided herein are small molecules for the induction of fibroblast proliferation and increased secretion or production of proteins. The small molecules described herein can be used for the promotion of skin regeneration. Also provided herein are methods for promoting skin regeneration and wound healing.

12 Claims, 9 Drawing Sheets

SMALL MOLECULES THAT PROMOTE SKIN REGENERATION

CROSS REFERENCE TO RELATED APPLICATION(S)

This application claims the benefit of priority under 35 U.S.C. §119(e) of U.S. Ser. No. 61/750,714, filed Jan. 9, 2013, the entire content of which is incorporated herein by reference.

BACKGROUND OF THE INVENTION

1. Field of the Invention

The present invention relates generally to skin regeneration and wound healing, and more specifically, to small molecule-mediated induction of dermal human fibroblast proliferation and increased protein production.

2. Background Information

The skin, the largest organ of the body in vertebrates, is composed of the epidermis and dermis with a complex nerve and blood supply. A third layer, the hypodermis, is composed mainly of fat and a layer of loose connective tissue. These three layers play an important role in protecting the body from any mechanical damage such as wounding.

The dermis, situated directly below the epidermis, constitutes the bulk of the skin and is composed of collagen with some elastin and glycosaminoglycans (GAGs). The major cell type present in the dermis is fibroblast, which is capable of producing remodeling enzymes such as proteases and collagenases that play an important role in the wound healing process.

Wound healing is a sequential mechanism and it is more specifically an event-driven process, whereby signals from one cell type set off cascades in other cell types, which propel the wound through the phases of healing. Adult wound healing is essentially a repair process, which normally exhibits scarring. Tissue repair begins immediately with fibrin clot deposition at the site of injury, preventing hemorrhage from damaged blood vessels. Circulating platelets then aggregate at the site of injury and various inflammatory mediators, such as PDGF, TGF-α and TGF-β, epidermal growth factor (EGF) and FGFs, are released. These molecules are also believed to play major roles downstream in the wound repair process.

The inflammatory response of adult tissues to wounding is characterized by an early influx of neutrophils whose numbers steadily increase and reach a maximum 24-48 hours post-wounding. As the neutrophil numbers begin to decline, macrophages take over and repopulate the wound site. Re-epithelialization also occurs at the same time, with keratinocytes migrating across the granulation tissue from deep within the dermis and the basal cells of the wound edge. As soon as the keratinocytes have re-established the barrier property of the skin, they resume a basal cell phenotype upon contact inhibition and differentiate into a stratified squamous keratinizing epidermis.

The final phases of the inflammatory response and epithelialization coincide with the migration of fibroblasts and endothelial cells and the formation of granulation tissue. Angiogenesis and fibroplasia then take place, with fibroblasts becoming the dominant cell type, laying down collagen and ECM. Remodeling of collagen occurs using matrix metalloproteinases produced by the fibroblasts and macrophages.

Dermal fibroblasts require far higher concentrations of fibroblast growth factor (FGF) in order to undergo cell replication and are responsible for creating the ECM, which organizes the stratified squamous epithelial cells of the epidermis into a unified tissue. Furthermore, dermal fibroblasts create long fibrous bands of connective tissue which anchor the skin to the fascia of the body. Without dermal fibroblasts, a wound site cannot regenerate extracellular matrix and epidermis skin cells cannot proliferate over the wound site. Therefore, without dermal fibroblasts the skin cannot properly recover from injury.

In humans, skin represents approximately one-tenth of the body mass, and damage such as trauma, disease, burn or surgery to a part of this major organ has dramatic consequences. Tissue-engineered skin substitutes are used in combating acute and chronic skin wounds. Tissue engineering aims to regenerate new biological material for replacing diseased or damaged tissues or organs. To achieve this, not only is a source of cells required, but also an artificial extracellular matrix (ECM) upon which the cells can be supported.

Natural biopolymers such as collagen and fibronectin have been investigated as potential sources of biomaterial to which cells can attach. The first generation of degradable polymers used in tissue engineering were adapted from other surgical uses and have drawbacks in terms of mechanical and degradation properties. This has led to the development of synthetic degradable gels primarily as a way to deliver cells and/or molecules in situ, the so-called smart matrix technology. Tissue or organ repair is usually accompanied by fibrotic reactions that result in the production of a scar. Certain mammalian tissues, however, have a capacity for complete regeneration without scarring; good examples include embryonic or fetal skin and the ear of the MRL/MpJ mouse. Investigations of these model systems revealed that in order to achieve such complete regeneration, the inflammatory response is altered such that the extent of fibrosis and scarring is diminished.

Dermal fibroblasts are a dynamic population of cells that have a key role in ECM deposition, epithelial-mesenchymal interactions and wound healing. Fibroblasts are readily cultured in the laboratory and incorporation of fibroblasts into tissue-engineered skin substitutes has produced encouraging results including symptomatic pain relief, more rapid healing of acute and chronic wounds, less scarring and better cosmetic results. However, at the present time, there are no models of bioengineered skin that completely replicate the anatomy, physiology, biological stability or aesthetic nature of uninjured skin.

Various tissue-engineered skin products need to be compared in multicenter clinical trials as this would enable the identification of specific products for particular clinical applications. This could potentially lead to a reduction in their costs following increased use of the specified product. In addition, a combination of tissue-engineered skin substitutes with cytokines and growth factors may in the future be used to enhance wound healing as well as afford the possibility of incorporating defensins for antimicrobial benefit. A need therefore exists for novel approaches to generate a skin replacement whose materials technology is based not only upon intelligent design, but also upon the molecules involved in the process of regeneration.

SUMMARY OF THE INVENTION

The present invention is based on the seminal discovery that certain small molecules induce fibroblast proliferation and/or increase protein production.

Provided herein is a method of inducing fibroblast proliferation in a subject. The method includes administering to a subject an effective amount of a small molecule that induces fibroblast proliferation. In certain aspects, the small molecule is SL 327, ABT 702, fenobam, SX 011, physostigimine hemisulfate or NBQX.

Also provided herein is a method for increasing protein secretion in a subject. The method includes administering to a subject an effective amount of a small molecule that increases protein secretion.

In certain aspects, the growth factor is EGF, FGF7/KGF, TGFβ or collagen I. In other aspects, the small molecule is CY 208-243, CD 439, T 0156 hydrochloride, CD 1530, PSB 06126, prostaglandin E2, LY 294002 hydrochloride, KB-R7943 mesylate, proxyfan oxalate, m-3M3FBS, dipyridamole, methyllycaconitine citrate, WIN 64338, clemastine fumarate or cilostazol.

In one embodiment, the protein is EGF and the small molecule is selected from the group consisting of CY 208-243, CD 439, T 0156 hydrochloride, CD 1530 and PSB 06126. In another embodiment, the protein is FGF7/KGF and the small molecule is prostaglandin E2. In a further embodiment, protein is TGFβ and the small molecule is selected from the group consisting of LY 294002 hydrochloride, KB-R7943 mesylate, proxyfan oxalate and m-3M3FBS. In yet a further embodiment, the protein is collagen I and the small molecule is selected from the group consisting of dipyridamole, methyllycaconitine citrate, WIN 64338, clemastine fumarate and cilostazol.

A method for promoting skin regeneration is provided herein. The method includes administering to a subject an effective amount of a compound that induces fibroblast proliferation or that increases protein secretion. In certain aspects, the protein is EGF, FGF7/KGF, TGFβ or collagen I. In certain aspects, the small molecule that induces fibroblast proliferation is SL 327, ABT 702, fenobam, SX 011, physostigimine hemisulfate or NBQX. In other aspects, the small molecule that increases protein secretion is CY 208-243, CD 439, T 0156 hydrochloride, CD 1530, PSB 06126, prostaglandin E2, LY 294002 hydrochloride, KB-R7943 mesylate, proxyfan oxalate, m-3M3FBS, dipyridamole, methyllycaconitine citrate, WIN 64338, clemastine fumarate or cilostazol.

In certain embodiments, subject is a human. In other embodiments, the cells are in cell culture in vitro. Such cells include human dermal fibroblast (hDF) cells.

DETAILED DESCRIPTION OF THE INVENTION

Figure 1:
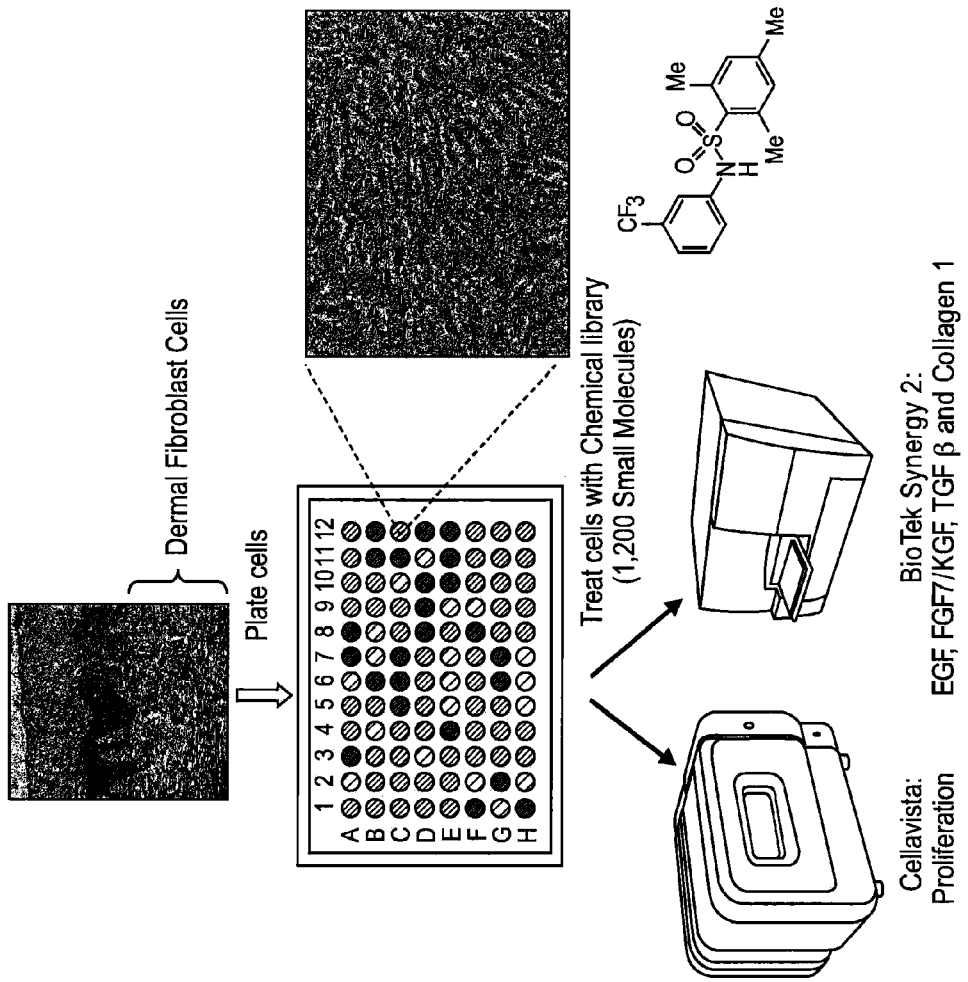
FIG. 1 is a schematic representation of high-throughput dermal fibroblast assay screens.

Dermal fibroblasts are skin cells responsible for the production of collagen that contribute to the formation of connective tissue fibers and growth factors that promote skin-barrier integrity and wound healing. In normal wound healing, fibroblasts are recruited from the surrounding intact tissue into the granulation tissue to proliferate and regenerate a new dermal layer in response to various factors presented in the wound fluid. During normal aging, dermal fibroblasts lose both the ability to proliferate and the capacity to secrete growth factors (e.g., EGF, FGF7/KGF, TGFβ, Collagen) involved in normal wound healing. A high-throughput screen designed to identify small molecules that promote fibroblast proliferation and increase secretion of proteins (e.g., EGF, FGF7/KGF, TGFβ, Collagen) is described herein.

A growth factor is a naturally occurring substance capable of stimulating cellular growth, proliferation and cellular differentiation. Growth factors are important for regulating a variety of cellular processes. Growth factors typically act as signaling molecules between cells. Examples are cytokines and hormones that bind to specific receptors on the surface of their target cells. They often promote cell differentiation and maturation, which varies between growth factors. For example, bone morphogenic proteins stimulate bone cell differentiation, while fibroblast growth factors and vascular endothelial growth factors stimulate blood vessel differentiation (angiogenesis). Examples of growth factors and families of growth factors include, but are not limited to: Adrenomedullin (AM), Angiopoietin (Ang), Autocrine motility factor, Bone morphogenetic proteins (BMPs), Brain-derived neurotrophic factor (BDNF), Epidermal growth factor (EGF), Erythropoietin (EPO), Fibroblast growth factor (FGF), Glial cell line-derived neurotrophic factor (GDNF), Granulocyte colony-stimulating factor (G-CSF), Granulocyte macrophage colony-stimulating factor (GM-CSF), Growth differentiation factor-9 (GDF9), Hepatocyte growth factor (HGF), Hepatoma-derived growth factor (HDGF), Insulin-like growth factor (IGF), Migration-stimulating factor, Myostatin (GDF-8), Nerve growth factor (NGF) and other neurotrophins, Platelet-derived growth factor (PDGF), Thrombopoietin (TPO), Transforming growth factor alpha (TGF-α), Transforming growth factor beta (TGF-β), Tumor necrosis factor-alpha (TNF-α), Vascular endothelial growth factor (VEGF), Wnt Signaling Pathway, placental growth factor (PlGF), Fetal Bovine Somatotrophin (FBS), IL-1, IL-2, IL-3, IL-4, IL-5, IL-6, IL-7, bFGF and VEGF.

Fibroblasts secrete soluble factors that diffuse to the overlying epidermis and influence keratinocytes in a paracrine manner and release cytokines and growth factors that have autocrine and paracrine effects. Autocrine activity includes the transforming growth factor (TGF)-β-induced synthesis and secretion of connective tissue growth factor which promotes collagen synthesis as well as fibroblast proliferation. Paracrine activity affects keratinocyte growth and differentiation, specifically through fibroblast secretion of keratinocyte growth factor (KGF), granulocyte-macrophage colony-stimulating factor, interleukin (IL)-6 and fibroblast growth factor (FGF)-10. In response, keratinocytes synthesize IL-1 and parathyroid hormone-related peptide which, in turn, stimulate fibroblasts to produce KGF and thus a double paracrine loop exists. Furthermore, keratinocytes cultured alone express IL-1 relatively weakly but when co-cultured with fibroblasts show increased expression of IL-1 and c-Jun. Therefore, fibroblasts incorporated into a dermal substrate play a role in producing ECM and stimulatory growth factors, which provides the optimum environment to support epidermis formation and to facilitate wound healing.

Fibroblast density is an important factor to consider for the development of normal epidermal morphology and keratinocyte differentiation and that the optimum density still needs to be established. Fibroblasts also contribute to basement membrane formation partly by producing collagen types IV and VII, laminin 5 and nidogen, but also through the secretion of cytokines that stimulate keratinocytes to produce basement membrane components. TGF-β secreted by fibroblasts induces the synthesis of collagen types IV and VII by keratinocytes.

Neovascularization and lymphangiogenesis are also important processes for the maintenance of normal skin homeostasis and wound healing, for which fibroblasts have an important paracrine role. Members of the vascular endothelial growth factor (VEGF) family include VEGF-A, -B, -C and -D, which are produced by normal human fibroblasts and are important in regulating vascular and lymphatic endothelial cell proliferation through specific receptors. VEGF-A is well known to be involved in the activation of resident endothelial cells and endothelial progenitor cells capable of vasculogenesis; VEGF-B is less mitogenic for endothelial cells while VEGF-C and -D have the same receptor specificity, binding to VEGF receptor 2 (VEGF-R2) to mediate angiogenesis and binding to VEGF-R3 to influence lymphangiogenesis.

FGF-1 encourages the body's own adhesive tissue to develop and effectively seal the wound, thereby stymieing infection and mitigating scar formation. Using FGF to stimulate fibroblast activity is an effective means of sealing tissue due to the robust nature of collagen which makes up connective tissue. To seal together tissues the human body uses collagen and elastin to obtain superior shear strength. Type I collagen, which includes collagen strands bundled into strong fibrils has a unique tri-helical structure that increases its structural integrity.

The following examples are intended to illustrate but not limit the invention.

Example 1

High-Throughput Proliferation Screening Assay for Proliferation of Human Dermal Fibroblasts (hDF)

For the proliferation assay, human dermal fibroblast (hDF) were plated into 96 well Black/Clear bottom tissue-culture treated plates (Corning) at 1,000 cells/well in DMEM (Gibco) 15% FBS (HyClone). On the next day cells were treated with the small molecule library (Torcris 1120 Biologically Active Compounds) at 2.5 µM final concentration. After 3 days of treatment, cells were fixed and stained with DAPI and analyzed using Roche Cellavista High-Content Imaging System (see FIG. 1).

Figure 2:
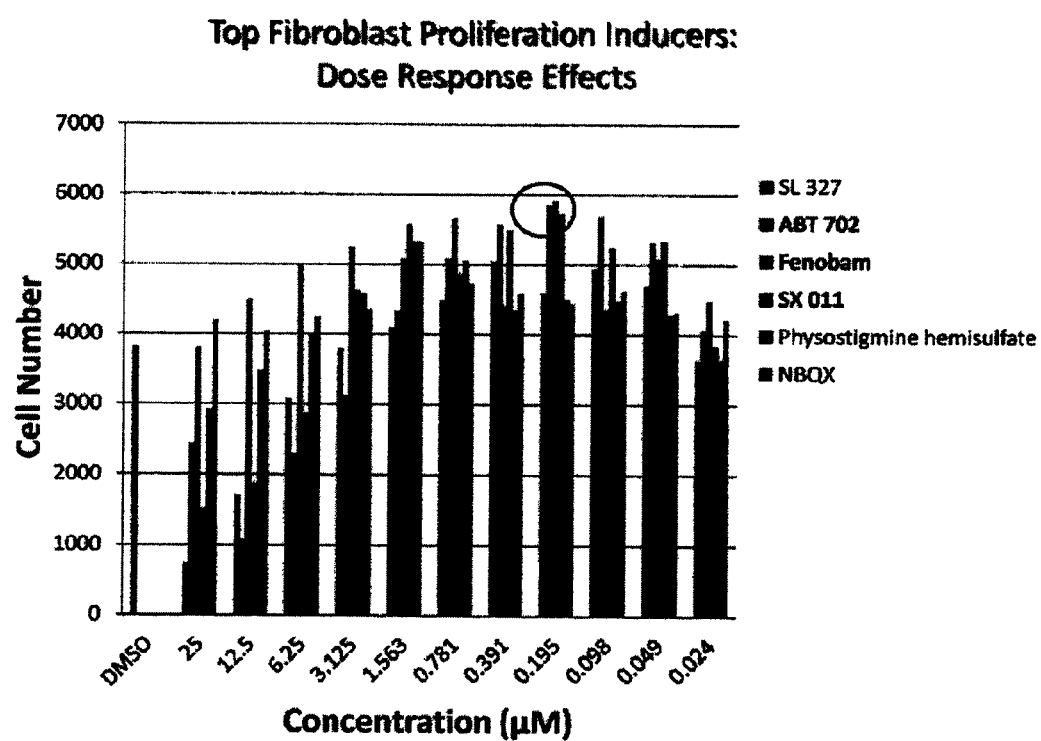
FIG. 2 is a graphic representation of small molecules that induce fibroblast proliferation as a function of dose.

From the high-throughput proliferation screening assay it was found that ABT702 dihydrochloride (Adenosine kinase Antagonist), Fenobam (mGlu$_5$ Receptor Antagonist) and SX 011 (p38 MAPK Antagonist), induced the highest proliferation level in hDFs at concentration of 200 nM (see FIG. 2).

Example 2

High-Throughput Screening Assay for FGF7 Production

For FGF7 production assay hDFs were plated into 96 well Clear tissue-culture treated plates (Falcon) at 19,000 cells/well in DMEM (Gibco) 1× N2/B27 Supplement (Invitrogen). On the next day cells were treated with the small molecule library (Torcris 1120 Biologically Active Compounds) at 2.5 µM final concentration. After 3 days of treatment, supernatants were collected and analyzed for FGF7 content using FGF7 Human ELISA Kit (Abcam) and with BioTek Synergy 2 Multi-Detection Microplate Reader (see FIG. 1).

Figure 3:
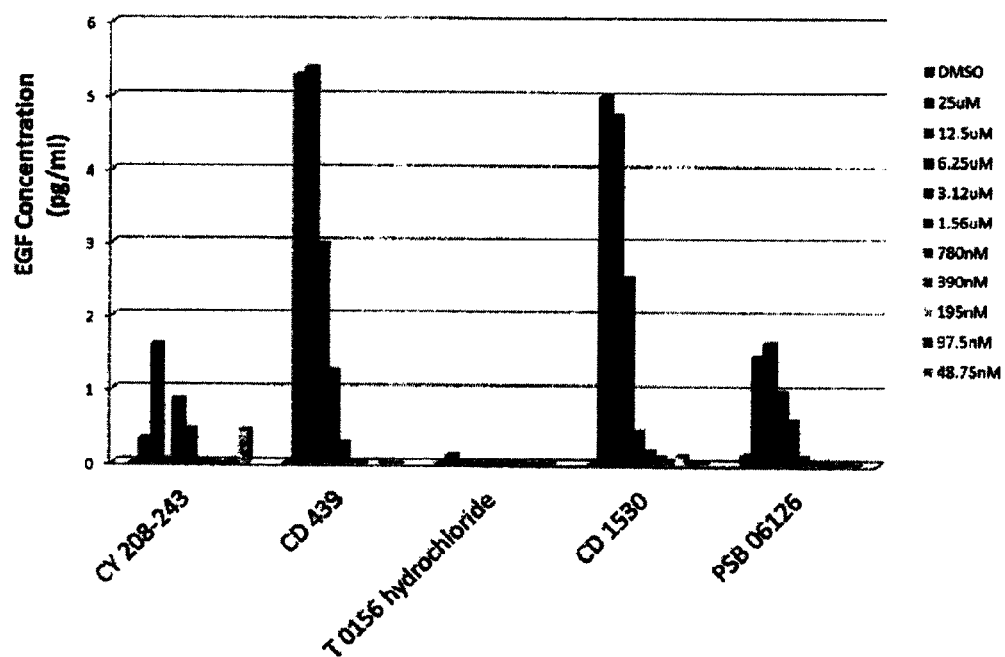
FIG. 3 is a graphic representation of small molecules that induce EGF expression as a function of dose.

From the high-throughput screening assay for FGF7 production assay it was found that Prostaglandin E$_2$ at concentration of 25 µM induced the highest production level of FGF7 in hDFs (see FIG. 3).

Example 3

High-Throughput Screening Assay for TGFβ1 Production

For TGFβ1 production assay hDFs were plated into 96 well Clear tissue-culture treated plates (Falcon) at 19,000 cells/well in DMEM (Gibco) 1× N2/B27 Supplement (Invitrogen). On the next day cells were treated with the small molecule library (Torcris 1120 Biologically Active Compounds) at 2.5 µM final concentration. After 3 days of treatment, supernatants were collected and analyzed for TGFµ1 content using TGFµ1 Human ELISA Kit (Abeam) and with BioTek Synergy 2 Multi-Detection Microplate Reader (see FIG. 1).

Figure 4:
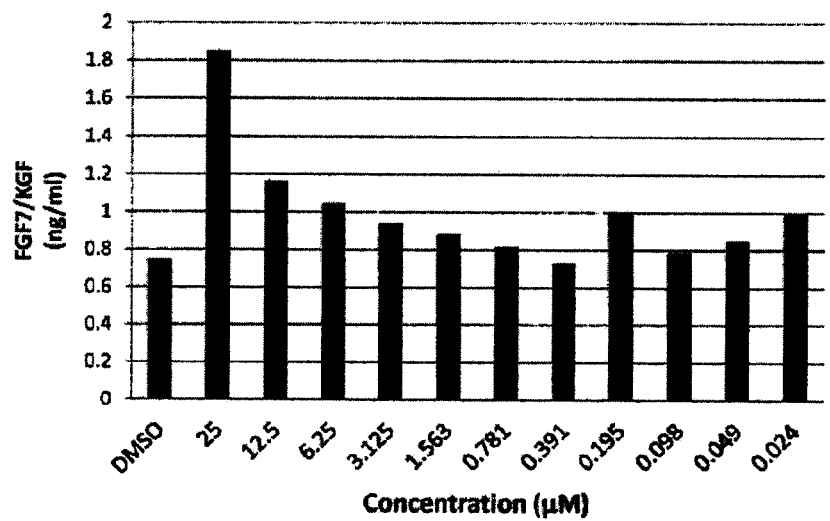
FIG. 4 is a graphic representation of small molecules that induce FGF7/KGF expression as a function of dose.

From the high-throughput Screening Assay for TGFβ1 production assay it was found that Proxyfan Oxalate (Histamine H$_3$ receptor Signaling Agonist) at concentration of 24 nM, m-3M3FBS (Phospholipase C Signaling) at concentration of 24 nM, KB-R7943 mesylate at concentration of 1.6 µM and LY294002 Hydrochloride at concentration of 98 nM induced the highest production level of TGFµ1 in hDFs (see FIG. 4).

Example 4

High-Throughput Screening Assay for EGF Production

For EGF production assay hDFs were plated into 96 well Clear tissue-culture treated plates (Falcon) at 19,000 cells/well in DMEM (Gibco) 1× N2/B27 Supplement (Invitrogen). On the next day cells were treated with the small molecule library (Torcris 1120 Biologically Active Compounds) at 2.5 µM final concentration. After 3 days of treatment, supernatants were collected and analyzed for EGF content using EGF Human ELISA Kit (Abeam) and with BioTek Synergy 2 Multi-Detection Microplate Reader (see FIG. 1).

Figure 5:
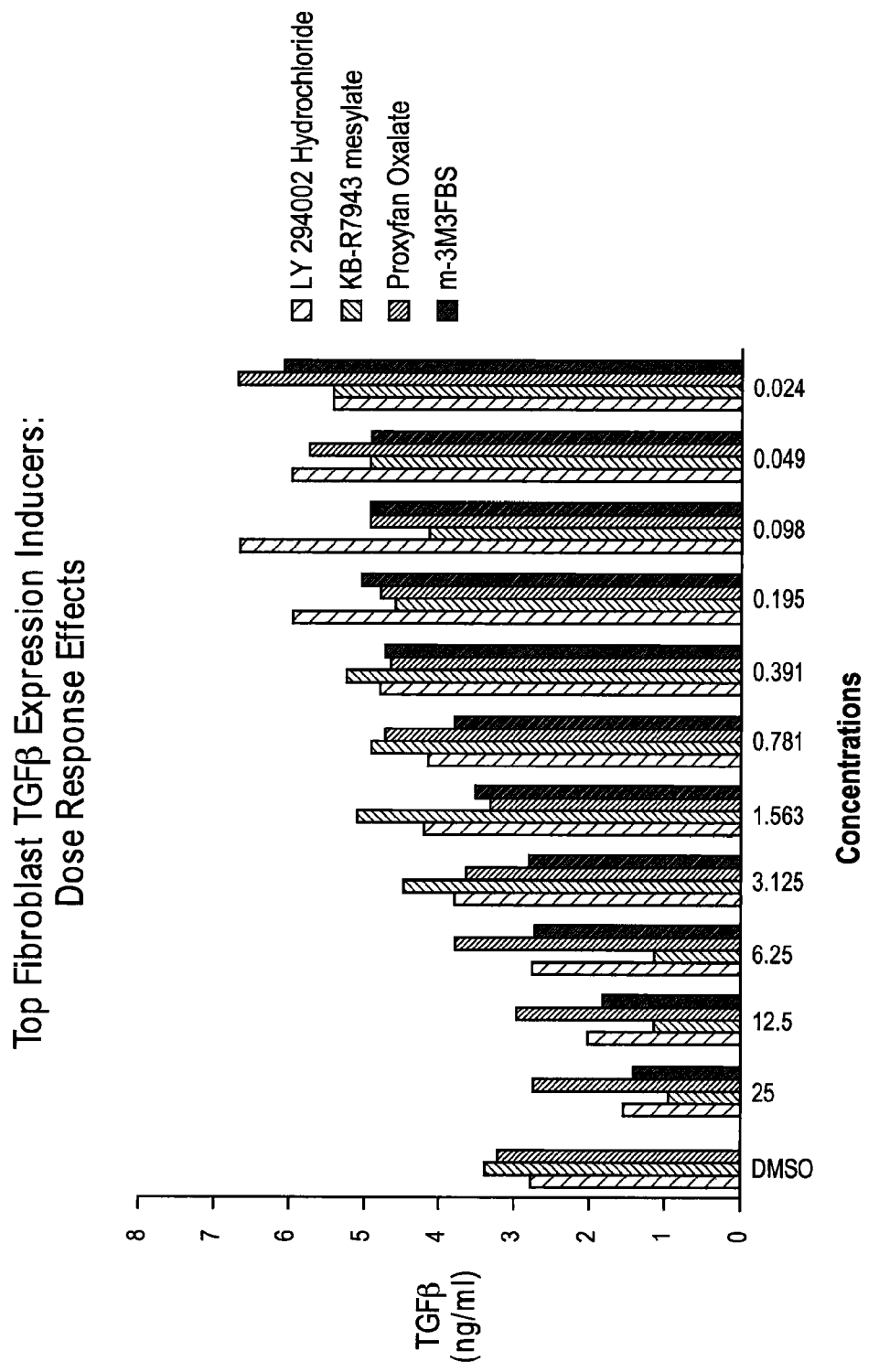
FIG. 5 is a graphic representation of small molecules that induce TGFβ expression as a function of dose.
Figure 6:
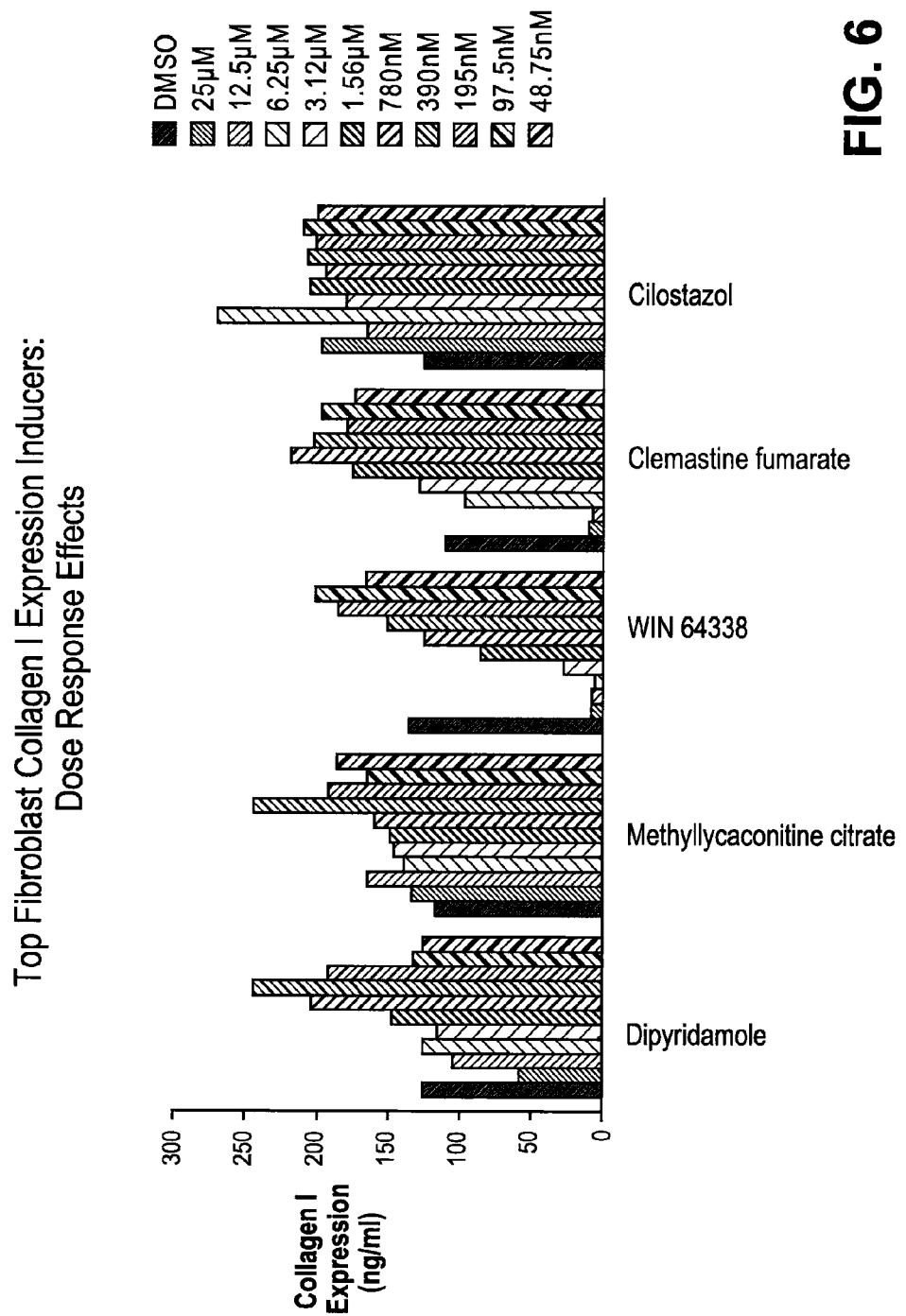
FIG. 6 is a graphic representation of small molecules that induce collagen I expression as a function of dose.
Figure 7:
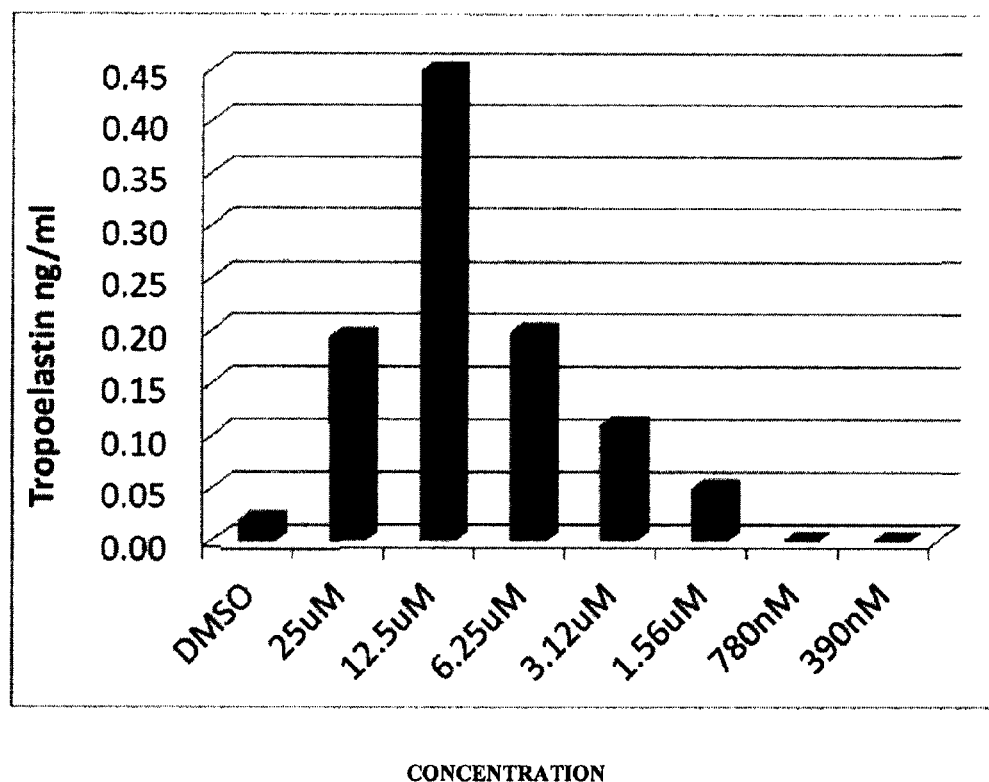
FIG. 7 graphically depicts induced elastin protein expression.
Figure 8:
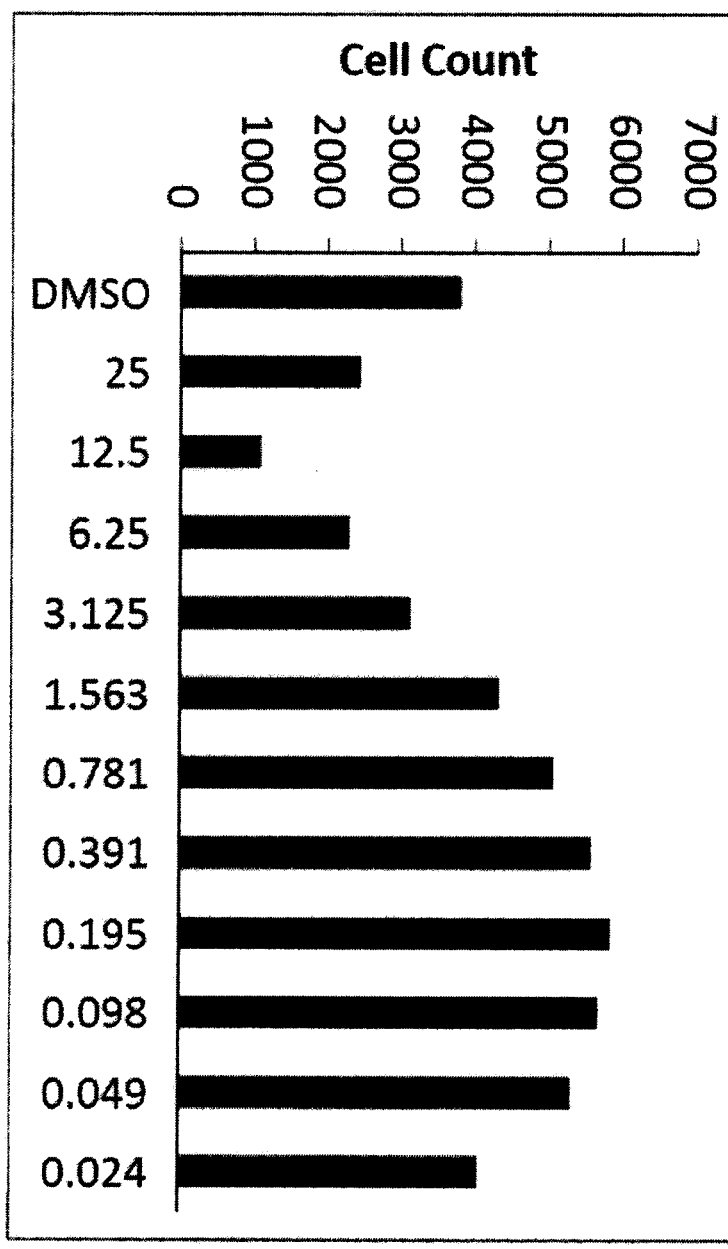
FIG. 8 is a graphic representation of cellular toxicity as a function of dimethylsulfoxide.
Figure 9:
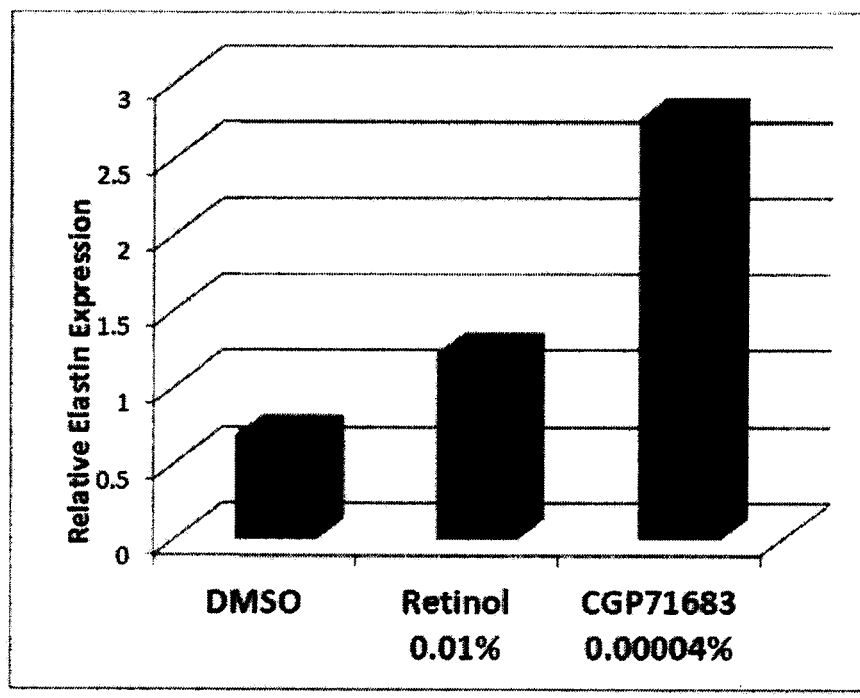
FIG. 9 is a bar graph that represents relative elastin expression as a function of DMSO, retinol and small molecule CGP71683.
Figure 10:
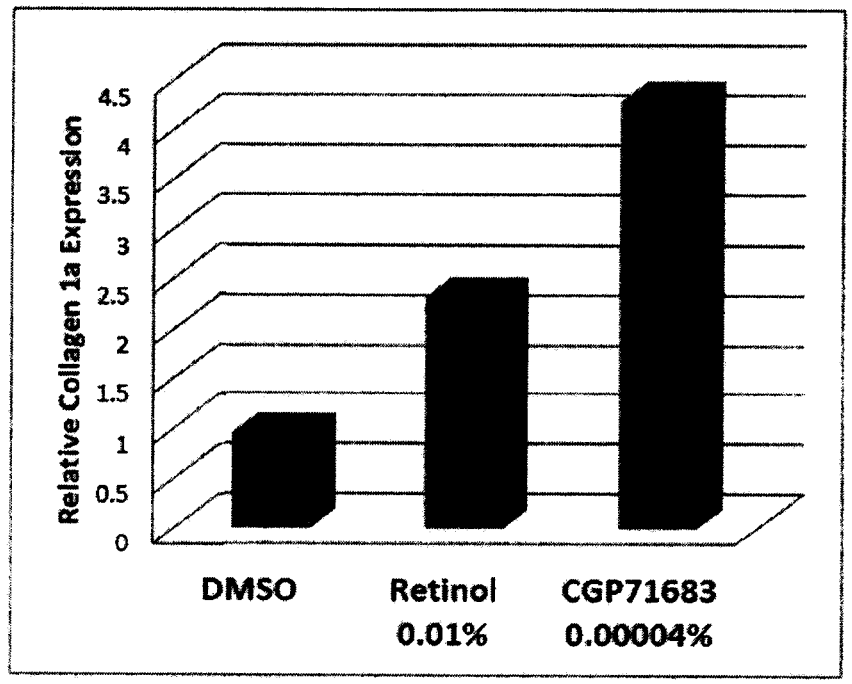
FIG. 10 is a bar graph that represents relative collagen 1a expression as a function of DMSO, retinol and small molecule CGP71683.

From the high-throughput Screening Assay for EGF production assay it was found that CD 437 and CD 1530 (Retinoid RAR Signaling Agonists) at concentrations of 25 and 12.5 µM, CY 208-243 (Dopamine D1 receptor Agonist) at concentrations of 12.5 µM and PSB 06126 (NTPDase 3 Antagonist) at concentration of 12.5 µM, induced the highest production level of EGF in hDFs (see FIG. 5).

Example 5

High-Throughput Screening Assay for Collagen Type 1 Production

For Collagen Type 1 production assay hDFs were plated into 96 well clear tissue-culture treated plates (Falcon) at 5,000 cells/well in DMEM (Gibco) 1× N2 Supplement (Invitrogen). On the next day cells were treated with the small molecule library (Torcris 1120 Biologically Active Compounds) at 2.5 µM final concentration. After 3 days of treatment, supernatants were collected and analyzed for Collagen Type 1 content using Procollagen Type 1C-Peptide EIA Kit (Takara) and with BioTek Synergy 2 Multi-Detection Microplate Reader (see FIG. 1).

From the high-throughput Screening Assay for Collagen Type 1 assay it was found that Dipyridamole (Adenosine transport inhibitor) at concentration of 390 nM, Methyllycaconitine citrate (α7 neuronal nicotinic receptor antagonist) at concentration of 390 nM, Cilostazol (PDE3A Antagonist) at concentration of 6.25 µM, Clemastine fumarate (H4 receptor Antagonist) at concentration of 780 nM and WIN 64338 (Bradykinin B2 receptor antagonist) at concentration of 97.5 nM induced the highest production level of EGF in hDFs (see FIG. 1).

Although the invention has been described with reference to the above example, it will be understood that modifications and variations are encompassed within the spirit and scope of the invention. Accordingly, the invention is limited only by the following claims.

What is claimed is:

1. A method of increasing secretion of collagen in a subject, comprising administering to a subject an effective amount of a compound that increases secretion of collagen, wherein the compound is selected from the group consisting of CY 208-243, CD 439, T 0156 hydrochloride, CD 1530, PSB 06126, prostaglandin E2, LY 294002 hydrochloride, KB-R7943 mesylate, proxyfan oxalate, m-3M3FBS, dipyridamole, methyllycaconitine citrate, WIN 64338, clemastine fumarate and cilostazol.

2. The method of claim 1, wherein the subject is a human.

3. The method of claim 1, wherein the protein is collagen I.

4. The method of claim 1, wherein the compound is dipyridamole, methyllycaconitine citrate, WIN 64338, clemastine fumarate and cilostazol.

5. The method of claim 1, wherein the compound is selected from the group consisting of CY 208-243, CD 439, T 0156 hydrochloride, CD 1530 and PSB 06126.

6. The method of claim 1, wherein the compound is prostaglandin E2.

7. The method of claim 1, wherein the compound is selected from the group consisting of LY 294002 hydrochloride, KB-R7943 mesylate, proxyfan oxalate and m-3M3FBS.

8. The method of claim 1, wherein the compound is WIN 64338.

9. A method for promoting skin regeneration, comprising administering to a subject an effective amount of a compound that increases secretion of collagen, wherein the compound is selected from the group consisting of CY 208-243, CD 439, T 0156 hydrochloride, CD 1530, PSB 06126, prostaglandin E2, LY 294002 hydrochloride, KB-R7943 mesylate, proxyfan oxalate, m-3M3FBS, dipyridamole, methyllycaconitine citrate, WIN 64338, clemastine fumarate and cilostazol.

10. The method of claim 9, wherein the protein is collagen I.

11. The method of claim 9, wherein the compound is selected from the group consisting of dipyridamole, methyllycaconitine citrate, WIN 64338, clemastine fumarate and cilostazol.

12. The method of claim 9, wherein the compound is WIN 64338.

* * * * *